United States Patent [19]

Jacobs et al.

[11] 4,134,064

[45] Jan. 9, 1979

[54] METHOD AND APPARATUS FOR MAGNETICALLY DETERMINING THE $Gd_2O_3$ CONTENT IN $UO_2$ FUEL PELLETS WHILE ELIMINATING THE EFFECT OF FERROMAGNETIC IMPURITIES

[75] Inventors: Israel S. Jacobs, Schenectady; Joseph A. Lahut, Scotia, both of N.Y.; Leonard N. Grossman, Wilmington, N.C.

[73] Assignee: General Electric Company, Schenectady, N.Y.

[21] Appl. No.: 754,581

[22] Filed: Dec. 27, 1976

[51] Int. Cl.$^2$ ............................................. G01R 33/12
[52] U.S. Cl. .................................................... 324/201
[58] Field of Search ............................ 324/34 S, 34 R

[56] References Cited

U.S. PATENT DOCUMENTS

| | | | |
|---|---|---|---|
| 1,952,185 | 3/1934 | Smith | 324/34 R |
| 3,029,380 | 4/1962 | Nicol | 324/34 R |
| 3,787,761 | 1/1974 | Grossman et al. | 324/34 S |
| 3,913,009 | 10/1975 | Panasjuk et al. | 324/34 R |

OTHER PUBLICATIONS

Lee et al., Quartz Helix–Magnetic Susceptibility Balance–Rev. of Scin. Inst., vol. 29, No. 5, May, 1958, pp. 429–432.

Primary Examiner—Robert J. Corcoran
Attorney, Agent, or Firm—Lawrence D. Cutter; Joseph T. Cohen; Marvin Snyder

[57] ABSTRACT

A method and apparatus for magnetically determining the $Gd_2O_3$ content in $UO_2$ fuel pellets is described. The alternating current susceptibility of fuel pellets within a zircalloy cladding is measured using an ac inductive technique. Ferromagnetic impurity moments are saturated with a direct current magnetic field. Susceptibility increases with increasing $Gd_2O_3$ content when the ferromagnetic component is saturated in fields above 6 kOe.

13 Claims, 3 Drawing Figures

METHOD AND APPARATUS FOR MAGNETICALLY DETERMINING THE $Gd_2O_3$ CONTENT IN $UO_2$ FUEL PELLETS WHILE ELIMINATING THE EFFECT OF FERROMAGNETIC IMPURITIES

This invention relates to methods and apparatus for determining the concentration of burnable poisons in reactor fuel pellets. More specifically, this invention relates to a method and apparatus for measuring the $Gd_2O_3$ content in $UO_2$ fuel pellets wherein ferromagnetic impurity moments are saturated with a dc bias magnetic field.

Uranium oxide fuel pellets in nuclear reactors will contain gadolinia ($Gd_2O_3$) as a burnable poison in increments of 0.5 w/o from 0.0 w/o to 8.0 w/o. The pellets are assembled into fuel rods and are clad, for example, with zircalloy. Each completed fuel rod may contain up to six zones with different gadolinia concentrations. A method is required to determine that the correct concentration and distribution of gadolinia is present within a completed fuel rod assembly.

Magnetically $UO_2$ and $Gd_2O_3$ are paramagnetic and have susceptibilities, X, of $8.74 \times 10^{-6}$ emu/g-Oe and $147 \times 10^{-6}$ emu/g-Oe, respectively. The processing of fuel pellets for use in reactors typically introduces up to 500 ppm of elemental iron and/or ferromagnetic alloys as impurities.

SUMMARY OF THE INVENTION

The magnetic susceptibility dM/dH of uranium oxide fuel pellets has been found to increase with the addition of gadolinia. Ferromagnetic inclusions in fuel pellets complicate the gadolinia determination by adding susceptibilities proportional to the ferromagnetic content. The susceptibility of ferromagnetic inclusions decreases, however, at high applied fields.

The gadolinia content of fuel pellets may be nondestructively determined by measuring the alternating current susceptibility using an inductive technique. Ferromagnetic inclusions are saturated with a high, direct current magnetic bias field which is applied during the susceptibility measurements.

It is, therefore, an object of this invention to provide nondestructive methods for determining the gadolinia concentration and distribution in uranium oxide fuel rods.

Another object of this invention is to minimize the measurement errors which occur when the chemical content of materials with ferromagnetic inclusions is determined from magnetic susceptibility measurements.

BRIEF DESCRIPTION OF THE DRAWINGS

The novel features believed characteristic of the present invention are set forth in the appended claims. The invention itself, together with further objects and advantages thereof, may best be understood by the following detailed description, taken in connection with the appended drawings in which:

DESCRIPTION OF THE PREFERRED EMBODIMENT

Figure 1:
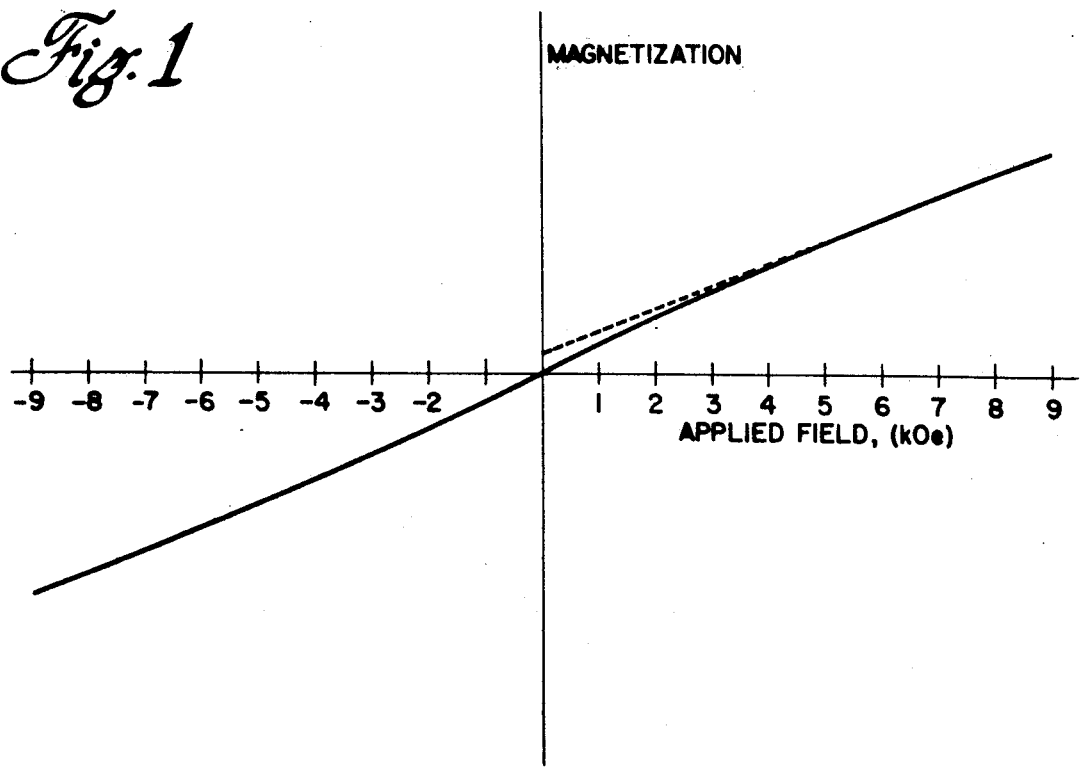
FIG. 1 is a magnetization curve of a fuel pellet.

The magnetic susceptibility of $UO_2$ is $8.74 \times 10^{-6}$ emu/g-Oe and that of $Gd_2O_3$ is $146.8 \times 10^{-6}$ emu/g-Oe. The susceptibility of $UO_2$ reactor fuel pellets will, therefore, increase for each 0.5 w/o addition of $Gd_2O_3$ in the $UO_2$, as $(U,Gd)O_2$. Ferromagnetic inclusions in the fuel pellets complicate the gadolinia determination by adding susceptibilities proportional to the ferromagnetic content. Fortunately, the susceptibility of ferromagnetic inclusions decreases dramatically at high applied fields. The solid curve of FIG. 1 shows an M/H curve of a fuel pellet containing 0.5 w/o $Gd_2O_3$ and ferromagnetic impurities (magnetically equivalent to 25 ppm iron). The dashed curve of FIG. 1 indicates the slope of the curve of a fuel pellet without iron impurities. The problem of ferromagnetic inclusions is, therefore, minimized by measuring the susceptibility of fuel pellets in a magnetic field which is large enough to saturate the ferromagnetic component. The saturating field may be produced by biasing the fuel pellet with a dc magnetic field component. It is evident from FIG. 1 that the magnitude of the bias field should be at least 4 kOe. In practice, a value of 5 kOe is satisfactory, but a larger value (e.g., 8 kOe) yields somewhat improved resolution.

Figure 2:
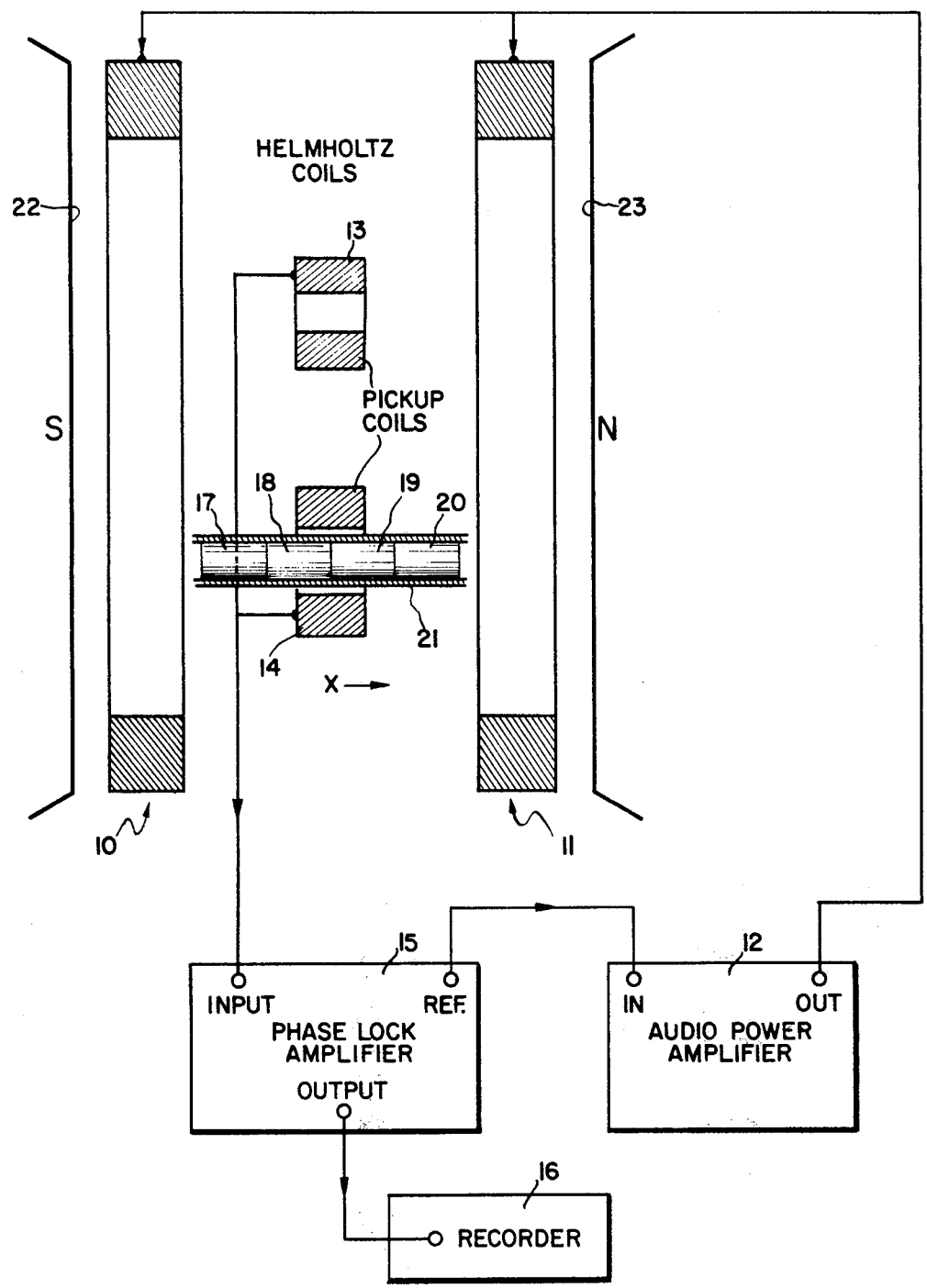
FIG. 2 is an apparatus for determining the gadolinia content in uranium oxide fuel rods.

FIG. 2 is apparatus for measuring the ac susceptibility of a fuel pellet using an inductive technique with a coaxial dc bias field. Techniques for inductive susceptibility measurements are described, for example, in Chapter 8 of *Magnetism and Mettalurgy*, edited by A. Berkowitz and E. Kneller, Academic Press, New York, 1969.

A pair of Helmholtz coils 10 and 11 are driven from an audio power amplifier 12 to produce a homogeneous ac magnetic field. Two coils 13 and 14, with substantially identical area.turns (NA) are placed between the Helmholtz coils 10 and 11 in the ac magnetic field. The coils 13 and 14 are connected in series opposition so that the voltage induced by the ac field approximately cancels. When a magnetic specimen is placed near one of the coils, an unbalanced voltage is produced which is proportional to the susceptibility of the sample dM/dH. The output voltage from the series opposed pickup coils 13 and 14 is fed to the input of a phase-lock amplifier 15. The output of the amplifier drives a recorder 16. The reference output signal from the phase-lock amplifier 15 is applied to the input of the audio power amplifier 12 to provide drive for the Helmholtz coils 10 and 11.

Four fuel pellets 17, 18, 19, and 20 were stacked in a zircalloy tube 21 which was translated along the axis of the pickup coil 14 during a measurement. The poles of a dc electromagnet 22 and 23 were aligned coaxially with the Helmholtz coils 10 and 11 and the pickup coils 13 and 14 to provide a dc bias field. This configuration gives maximum sample-to-coil coupling. Other coil and magnet configurations may also be used with a reduction in coupling efficiency.

The operating frequency was 82 Hz. The frequency is not critical but should be chosen to minimize mechanical resonances in the sample and measurement system and should be low enough to minimize skin effects and thus assure that the magnetic field will penetrate a nonmagnetic, conductive shield: that is, the zircalloy tubing 21. For zircalloy tubing with a resistivity of $7 \times 10^{-7}$ ohm-meters, the penetration depth δ at 80 Hz is approximately one-half centimeter.

By way of example, in typical experimental apparatus, each Helmholtz coil is approximately thirteen centimeters in diameter and comprises 525 turns of No. 30 Formex$^R$ coated wire. Fields produced were approximately 15 Oe at the operating frequency. The pickuo coils were approximately 1.4 centimeters inside diameter, approximately 0.25 centimeters high and included 2000 turns of wire. Four fuel pellets were measured containing, respectively, 0, 0.5, 2.5, and 4.0 weight percent $Gd_2O_3$ in $UO_2$. The pellets were approximately 1.06 centimeters in diameter and 1.08 centimeters long.

Figure 3:
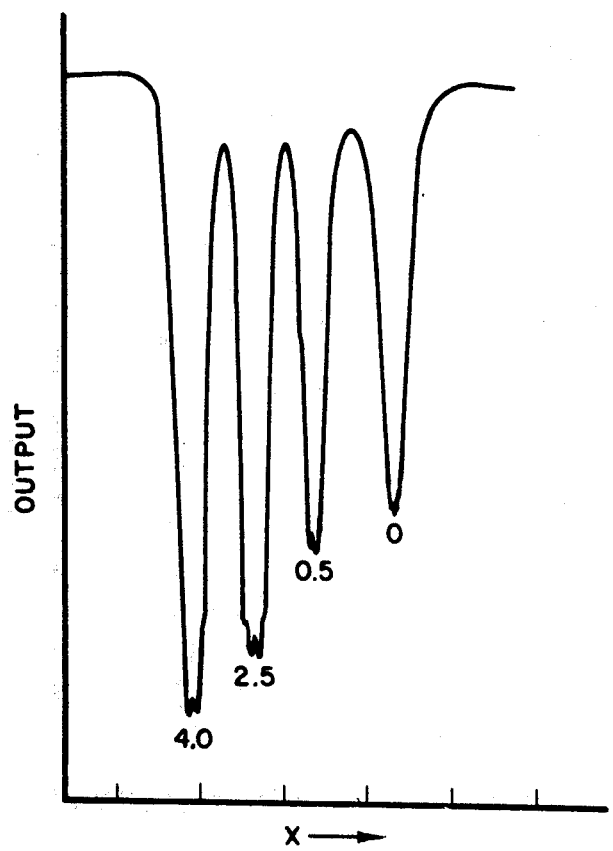
FIG. 3 is a plot of output signal vs. distance along a fuel rod, measured in accordance with the invention.

FIG. 3 is a curve of output signals from the phase-lock amplifier vs. position of the sample tube 21 for a tube containing the four fuel pellets described above. The gadolinia content of the fuel pellets and their relative position in the tube may be readily discerned.

Alternately, the dc bias magnetic field may be provided by an axial field permanent magnet disposed around one of the pickup coils.

The methods and apparatus of the present invention allow nondestructive determination of the gadolinia content and distribution in fuel rod assemblies. A dc bias field saturates ferromagnetic inclusions and eliminates errors which might, otherwise, interfere with measurement accuracy.

While the invention has been described in detail herein in accord with certain preferred embodiments thereof, many modifications and changes therein may be effected by those skilled in the art. Accordingly, it is intended by the appended claims to cover all such modifications and changes as fall within the spirit and scope of the invention.

The invention claimed is:

1. A method for determining the gadolinia content of fuel pellets which comprise gadolinia, urania, and ferromagnetic inclusions comprising the steps of:
    establishing a time invariant magnetic field sufficient to saturate said ferromagnetic inclusion;
    superimposing a homogeneous time alternating magnetic field on and substantially coaxial with said time invariant field;
    disposing a pair of series opposed pickup coils in said superimposed magnetic fields;
    coupling said fuel pellets to one of said pickup coils; and
    measuring an ac unbalance voltage induced on said series opposed coils by said fuel pellet; whereby the susceptibility of said fuel pellet is measured by an inductive technique and the measurement errors produced by said ferromagnetic inclusions are reduced to a negligible level.

2. The method of claim 1 wherein said time invariant field and said alternating field are coaxial.

3. The method of claim 2 wherein said pickup coils are solenoids and are disposed coaxially with said magnetic fields.

4. The method of claim 3 wherein said pellets are coupled coaxially with said pickup coil.

5. The method of claim 3 wherein said alternating magnetic field is produced by energizing a pair of Helmholtz coils with an audio frequency signal.

6. The method of claim 5 wherein said unbalance voltage is detected coherently with said audio signal.

7. The method of claim 6 wherein said fuel pellet is contained in a nonmagnetic, conducting tube and wherein the frequency of said audio signal is chosen to produce a penetration depth greater than the thickness of a wall of said tube.

8. An improved method for measuring the susceptibility of a sample pellet by an ac inductive technique which includes connecting a pair of pickup coils in series opposition, coupling said pellet to one of said pickup coils; immersing said pickup coils in a homogeneous, time alternating, magnetic field; and measuring an unbalance voltage induced in said coils by the presence of said pellet wherein said pellet contains ferromagnetic inclusions; and the improvement comprises:
    immersing said pellet in a time invariant magnetic field, coaxial with said alternating field, of sufficient magnitude to saturate the ferromagnetic inclusions.

9. Apparatus for determining the gadolinia content of reactor fuel pellets comprising:
    a first magnetic pickup coil;
    a second magnetic pickup coil connected in series opposition with said first pickup coil;
    means for immersing said pickup coils in a homogeneous time alternating magnetic field;
    a reactor fuel pellet comprising uranium oxide, gadolinia, and ferromagnetic inclusions, coupled to said first pickup coil;
    means for detecting unbalanced voltages induced in the series circuit of said pickup coils by said fuel pellet; and
    means for immersing said fuel pellet in a time invariant bias magnetic field directed coaxially with said alternating field and of sufficient magnitude to saturate said ferromagnetic inclusions.

10. The apparatus of claim 9 wherein said means for producing said homogeneous alternating magnetic field comprise a pair of Helmholtz coils disposed about said pickup coils.

11. The apparatus of claim 10 wherein said means for producing said bias magnetic field comprise poles of a magnet disposed adjacent said Helmholtz coils.

12. The apparatus of claim 10 wherein said alternating magnetic field has a frequency of approximately 82 Hz.

13. The apparatus of claim 10 wherein said fuel pellet is enclosed in a nonmagnetic, conductive cladding and wherein the frequency of said alternating magnetic field is sufficiently low to ensure penetration of said cladding by magnetic field components.

* * * * *